US011391803B2

(12) United States Patent
Bilgic et al.

(10) Patent No.: US 11,391,803 B2
(45) Date of Patent: Jul. 19, 2022

(54) MULTI-SHOT ECHO PLANAR IMAGING THROUGH MACHINE LEARNING

(71) Applicant: THE GENERAL HOSPITAL CORPORATION, Boston, MA (US)

(72) Inventors: Berkin Bilgic, Boston, MA (US); Sohyun Han, Cambridge, MA (US); Stephen F. Cauley, Cambridge, MA (US); Lawrence L. Wald, Cambridge, MA (US); Kawin Setsompop, Charleston, MA (US)

(73) Assignee: The General Hospital Corporation, Boston, MA (US)

( * ) Notice: Subject to any disclaimer, the term of this patent is extended or adjusted under 35 U.S.C. 154(b) by 18 days.

(21) Appl. No.: 16/976,997

(22) PCT Filed: Mar. 4, 2019

(86) PCT No.: PCT/US2019/020569
§ 371 (c)(1),
(2) Date: Aug. 31, 2020

(87) PCT Pub. No.: WO2019/169393
PCT Pub. Date: Sep. 6, 2019

(65) Prior Publication Data
US 2021/0364589 A1    Nov. 25, 2021

Related U.S. Application Data

(60) Provisional application No. 62/637,655, filed on Mar. 2, 2018.

(51) Int. Cl.
*G01R 33/565* (2006.01)
*G01R 33/56* (2006.01)
(Continued)

(52) U.S. Cl.
CPC ..... *G01R 33/56509* (2013.01); *G01R 33/5608* (2013.01); *G01R 33/5616* (2013.01); *G06N 3/04* (2013.01); *G06T 11/008* (2013.01)

(58) Field of Classification Search
USPC ........................................................ 324/309
See application file for complete search history.

(56) References Cited

U.S. PATENT DOCUMENTS

2013/0182932 A1   7/2013   Chen
2017/0112449 A1   4/2017   Huang
(Continued)

FOREIGN PATENT DOCUMENTS

WO    2017092973 A1   11/2016
WO    2017223560 A1   12/2017

OTHER PUBLICATIONS

Chen NK, et al. A robust multi-shot scan strategy for high-resolution diffusion weighted MRI enabled by multiplexed sensitivity-encoding (MUSE). Neuroimage 2013;72:41-47.
(Continued)

*Primary Examiner* — Rodney E Fuller
(74) *Attorney, Agent, or Firm* — Quarles & Brady LLP (57) ABSTRACT

Systems and methods are provided for improving MRI data acquisition efficiency while providing more detailed information with high resolution and isotropic resolution without gaps. Improved data acquisition efficiency may be achieved by implementing a machine learning algorithm with a hardware processor and a memory to estimate imperfections in fast imaging sequences, such as a multi-shot echo planar imaging (MS-EPI) sequence. These imperfections, such as patient motion, physiological noise, and phase variations, may be difficult to model or otherwise estimate using standard physics-based reconstructions.

18 Claims, 6 Drawing Sheets

(51) Int. Cl.
  *G01R 33/561* (2006.01)
  *G06N 3/04* (2006.01)
  *G06T 11/00* (2006.01)

(56) References Cited

U.S. PATENT DOCUMENTS

| | | | |
|---|---|---|---|
| 2019/0128989 A1* | 5/2019 | Braun | G01R 33/56509 |
| 2020/0051239 A1* | 2/2020 | Braun | G06K 9/6269 |
| 2020/0294287 A1* | 9/2020 | Schlemper | G06T 11/008 |
| 2021/0181287 A1* | 6/2021 | Sommer | G01R 33/5608 |

OTHER PUBLICATIONS

He K, et al. Deep Residual Learning for Image Recognition. In: Proceedings of the IEEE conference on computer vision and pattern recognition. ; 2016. pp. 770-778.

International Searching Authority. International Search Report and Written Opinion for application PCT/US2019/020569, dated May 23, 2019. 16 pages.

Ioffe S, et al. Batch normalization: Accelerating deep network training by reducing internal covariate shift. Int. Conf. Mach. Learn. 2015:448-456.

Jeong H-K, et al. High-resolution human diffusion tensor imaging using 2-D navigated multishot SENSE EPI at 7 T. Magn. Reson. Med. 2013;69:793-802.

Zhang K, et al. Beyond a Gaussian Denoiser: Residual Learning of Deep CNN for Image Denoising. IEEE Trans. Image Process. [Internet] 2017;26:3142-3155.

\* cited by examiner

MULTI-SHOT ECHO PLANAR IMAGING THROUGH MACHINE LEARNING

CROSS-REFERENCE TO RELATED APPLICATIONS

This application represents the national stage entry of PCT International Application No. PCT/US2019/020569 filed Mar. 4, 2019, which claims the benefit of U.S. Provisional Patent Application Ser. No. 62/637,655 filed on Mar. 2, 2018, and entitled "Improved Multi-Shot Echo Planar Imaging through Machine Learning," which is herein incorporated by reference in its entirety.

STATEMENT REGARDING FEDERALLY SPONSORED RESEARCH

This invention was made with government support under EB02061302 and EB01733704 awarded by the National Institutes of Health. The government has certain rights in the invention.

BACKGROUND

MRI has demonstrated ability to provide exquisite contrast for non-invasive imaging. Slow data acquisition has always been a critical limiting factor in MRI. Slow acquisition increases sensitivity to patient motion induced image artifacts and reduces patient throughput and compliance. To limit acquisition time of each imaging scan, 2-dimensional imaging is used with thick slices and slice gaps. These gaps can result in missed information while thick slices necessitate additional scans if viewing in a different plane is desired, resulting in a lengthened MRI exam.

SUMMARY OF THE DISCLOSURE

The present disclosure addresses the aforementioned drawbacks by providing systems and methods using machine learning for improving MRI data acquisition efficiency while providing more detailed information with high and isotropic resolution without gaps. The systems and methods described in the present disclosure utilize a machine learning algorithm implemented with a hardware processor and a memory to estimate imperfections in fast imaging sequences and remove physiological artifacts caused by patient motion, respiration, cardiac pulsation, and other physiological noise sources.

In one configuration, a method is provided for reducing image artifacts using a magnetic resonance imaging system. The method includes acquiring image data of a subject using a magnetic resonance imaging (MRI) system implementing a rapid imaging sequence. The method also includes providing to a computer system a trained machine learning algorithm that has been trained on training data that includes corrupted image data and physiological artifacts in order to reconstruct images from image data such that the reconstructed images depict reduced physiological artifacts. The method also includes applying the acquired image data to the trained machine learning algorithm, and generating an output that includes one or more images reconstructed from the image data, where the one or more images depict reduced physiological artifacts.

In one configuration, a system is provided for reducing image artifacts using a magnetic resonance imaging system. The system includes a computer system configured to: i) acquire image data of a subject using a magnetic resonance imaging (MRI) system implementing a rapid imaging sequence; ii) implement a trained machine learning algorithm that has been trained on training data that includes corrupted image data and physiological artifacts in order to reconstruct images from image data such that the reconstructed images depict reduced physiological artifacts; and iii) apply the acquired image data to the trained machine learning algorithm to generate an output that includes one or more images reconstructed from the image data, and where the one or more images depict reduced physiological artifacts In one configuration, a non-transitory computer-readable medium storing instructions is provided. The instructions include a method for reducing image artifacts using a magnetic resonance imaging system. One or more instructions are included that, when executed by one or more processors, cause the one or more processors to: i) acquire image data of a subject using a magnetic resonance imaging (MRI) system implementing a rapid imaging sequence; ii) implement a trained machine learning algorithm that has been trained on training data that includes corrupted image data and physiological artifacts in order to reconstruct images from image data such that the reconstructed images depict reduced physiological artifacts; and iii) apply the acquired image data to the trained machine learning algorithm to generate an output that comprises one or more images reconstructed from the image data, and where the one or more images depict reduced physiological artifacts.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for improving MRI data acquisition efficiency while providing more detailed information with high and isotropic resolution without gaps. Using the systems and methods described in the present disclosure, the diagnostic power of MRI can be improved, motion sensitivity can be reduced, and patient throughput can be improved to make MRI more cost effective and more widely used in the clinic, particularly in time-sensitive situations.

The systems and methods described in the present disclosure utilize a machine learning algorithm implemented with a hardware processor and a memory to estimate imperfections in fast imaging sequences that are difficult to model or otherwise estimate using standard physics-based reconstructions. Such imperfections can include patient motion, physiological noise, phase variations, and the like. The systems and methods described in the present disclosure also provide physics-based image reconstruction with better initialization points, thus allowing synergistic combination with existing techniques.

One particular rapid imaging sequence that can be implemented with the systems and methods described in the present disclosure is multi-shot echo planar imaging (MS-EPI). EPI is a fast acquisition technique that can encode large volume (e.g., whole-brain) information in as short as two seconds, but does not lend itself to high-resolution structural imaging due to severe image distortion artifacts. These artifacts stem from the inhomogeneity of the MRI scanner's magnetic field, and can be mitigated using a multi-shot approach. MS-EPI encodes the image in several shorter segments, thus reducing the exposure to field inhomogeneity during the smaller acquisition windows. Although this mitigates image distortion, MS-EPI has been elusive because combining the multiple shots into a single image can be prohibitively difficult. For instance, the mismatch between the shots caused by physiological motion (respiration, cardiac pulsation, and patient motion) is too complicated to be modeled, and can often lead to severe image artifacts that preclude the usefulness of this method.

These physiological variations may be mitigated using additional "navigator" echoes, but at the cost of imaging efficiency and more complex and time consuming reconstruction, and in many cases significant remaining artifacts. Navigators provide 2-dimensional information on the shot-to-shot image phase variations, which are taken into account during conventional image reconstruction.

Navigation techniques have so far been applied to spin-echo (SE) acquisitions, where the physiological motion is largely compensated by the imaging sequence. But gradient-echo (GRE) applications have proved elusive since shot-to-shot phase variations can be much more severe. Alternatively, individual images from each shot can be reconstructed using parallel imaging, and shot-to-shot phase variations can be estimated based on the reconstructed images. This entails complicated post-processing and limits the maximum number of shots to around four.

Using the systems and methods described in the present disclosure, the need for additional navigator scans that reduce the scan efficiency—while not successfully removing artifacts in many cases—can be obviated. Moreover, using the systems and methods described in the present disclosure MS-EPI with GRE contrast can be achieved. GRE-based imaging sequences form the basis of the important susceptibility weighted imaging and functional MRI acquisitions, where the physiological motion is not compensated by the imaging sequence and is more severe than in SE-based imaging sequences.

A machine learning algorithm implemented with a hardware processor and memory may be used to learn and remove physiological artifacts. Many types of machine learning algorithms could be utilized to learn the shot-to-shot motion artifacts. As one non-limiting example, the machine learning algorithm can be a Residual Convolution Neural Network (CNN). These types of networks can be particularly useful for analyzing imaging data that have much fewer parameters that need to be trained than dense networks as a result of parameter sharing.

In some implementations, the machine learning algorithm can implement deep learning to add more layers. These additional layers can allow the network to describe complex interactions across many voxels due to the increase in receptive field (e.g., the number of input voxels that contribute to each output). A residual machine learning algorithm, such as a residual CNN, can be used such that rather than estimating the artifact-free image, the mapping between the corrupted images and motion artifacts can be learned instead. The optimization for such a residual mapping is easier than the original mapping between the corrupted and clean images, and deeper networks with improved accuracy can be trained this way.

Figure 4:
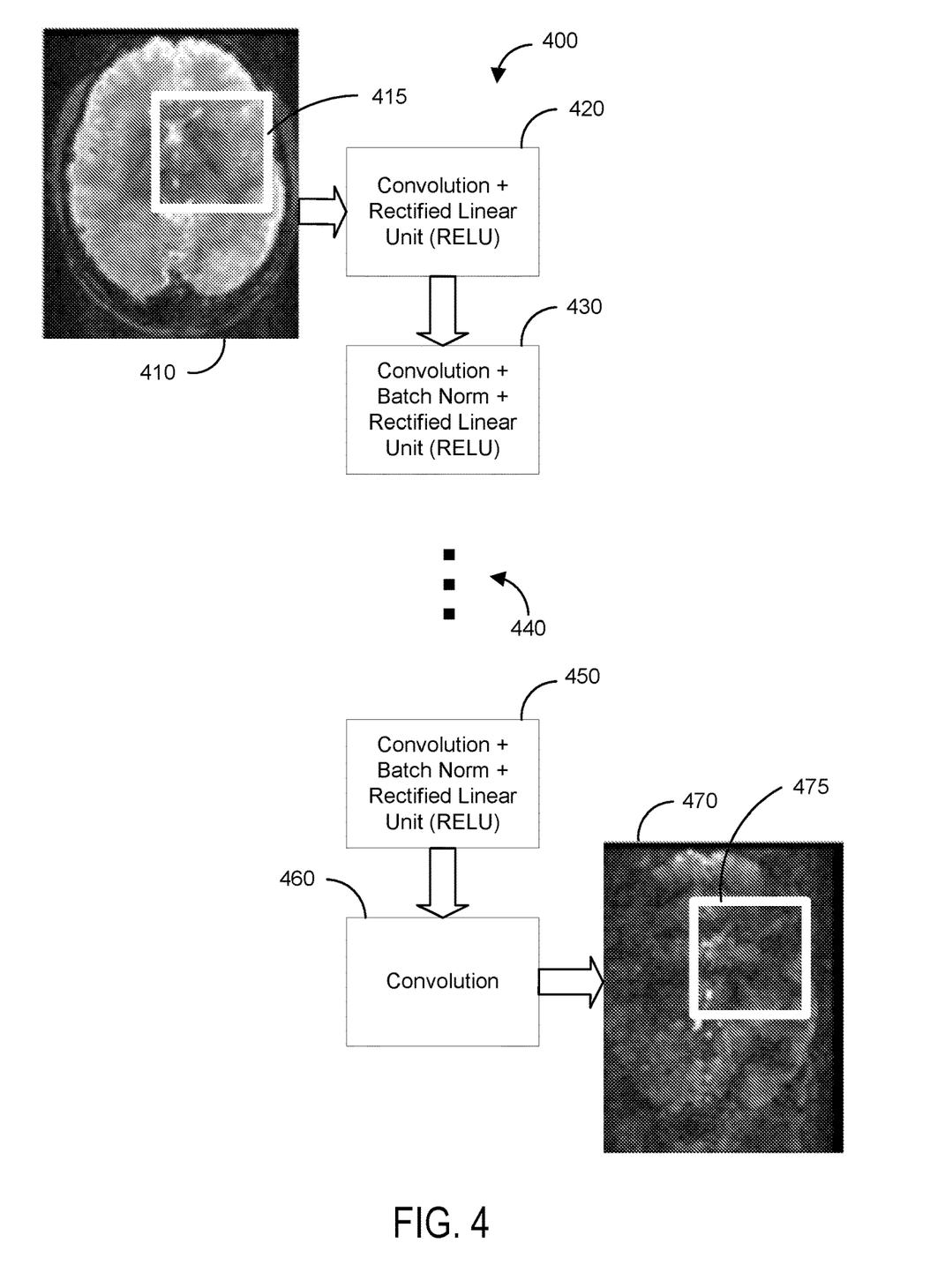
FIG. 4 illustrates an example of a convolutional neural network for improving multi-shot echo planar imaging.

As one non-limiting example, a Residual CNN with three types of layers can be constructed and implemented. The first layer can include convolution plus a rectified linear unit ("RELU"). As an example, this layer can include 64 filters with 3×3 convolutional kernels followed by RELU nonlinearity. The second layer can include convolution plus batch normalization and a RELU. As one example, the batch normalization can convert the samples to zero mean and unit variance and can provide higher learning rates. The last layer can include convolution, and as one example can include a single filter using a 3×3 convolutional kernel. An example of such a Residual CNN is shown in FIG. 4.

For training, pairs of corrupted MS-EPI data and the physiological motion artifacts can be created, and a patch-based approach can be implemented. A sliding window of size 51×51 (or other suitable size) can be used to extract training patches, and a CNN with a desired number of layers (e.g., 25 layers) can be trained. After estimating and removing the artifacts in each patch, an average over patches in a sliding window fashion can be computed to obtain the final reconstruction.

In some instances, training data may include simulated data. Corrupted MS-EPI data and physiological artifacts can be simulated in various ways. One approach can include acquiring in vivo single-shot EPI data time-series, during which physiological changes will naturally occur. After this, k-space data from different time points can be combined to synthesize a corrupted multi-shot acquisition, which will exhibit physiological artifacts. Because clean, single-shot data are also available, the artifact images could be obtained by subtracting the corrupted synthetic MS-EPI data from the clean single-shot images.

Figure 1A:
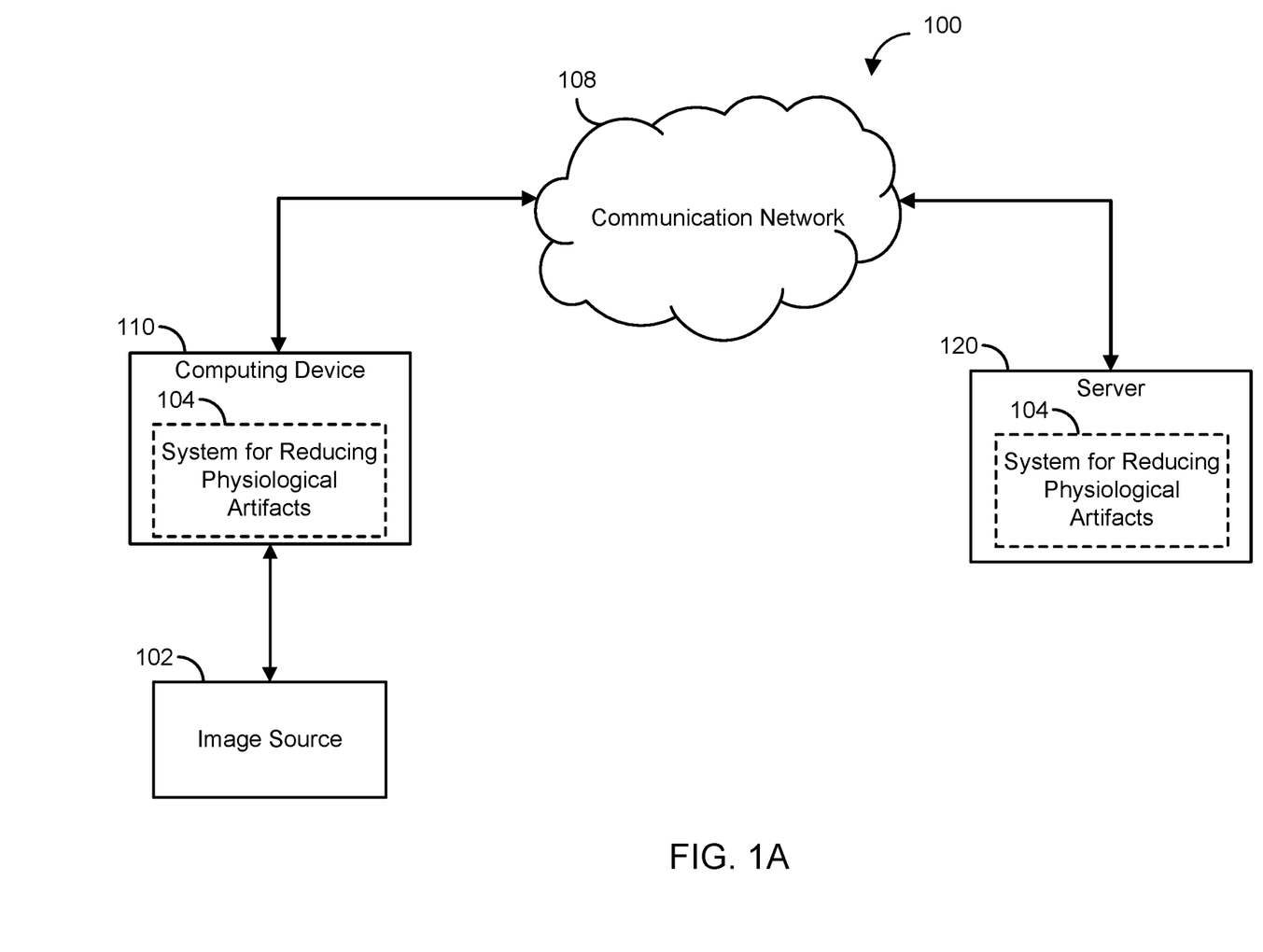
FIG. 1A is a block diagram of one non-limiting example system in accordance with the present disclosure.

Referring to FIG. 1A, an example of a system 100 in accordance with some aspects of the disclosed subject matter is provided. As shown in FIG. 1, a computing device 110 can receive multiple types of image data from an image source 102. In some configurations, the computing device 110 can execute at least a portion of a system for removing or reducing physiological artifacts from medical images 104. That is, as described above, medical imaging data, such as acquired from an MRI system, may be processed by a machine learning algorithm to remove image artifacts created by physiological motion.

Additionally or alternatively, in some configurations, the computing device 110 can communicate information about image data received from the image source 102 to a server 120 over a communication network 108, which can also include a version of a system for removing or reducing physiological artifacts from medical images 104.

In some configurations, the computing device 110 and/or server 120 can be any suitable computing device or combination of devices, such as a desktop computer, a laptop computer, a smartphone, a tablet computer, a wearable computer, a server computer, a virtual machine being executed by a physical computing device, etc.

In some configurations, the image source 102 can be any suitable source of medical image data, such as an MRI, CT, ultrasound, PET, SPECT, x-ray, or another computing device (e.g., a server storing image data), and the like. In some configurations, the image source 102 can be local to the computing device 110. For example, the image source 102 can be incorporated with the computing device 110 (e.g., the computing device 110 can be configured as part of a device for capturing and/or storing images). As another example, the image source 102 can be connected to the computing device 110 by a cable, a direct wireless link, or the like. Additionally or alternatively, in some configurations, the image source 102 can be located locally and/or remotely from the computing device 110, and can communicate image data to the computing device 110 (and/or server 120) via a communication network (e.g., the communication network 108).

In some configurations, the communication network 108 can be any suitable communication network or combination of communication networks. For example, the communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some configurations, the communication network 108 can be a local area network, a wide area network, a public network (e.g., the Internet), a private or semi-private network (e.g., a corporate or university intranet), other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 1B:
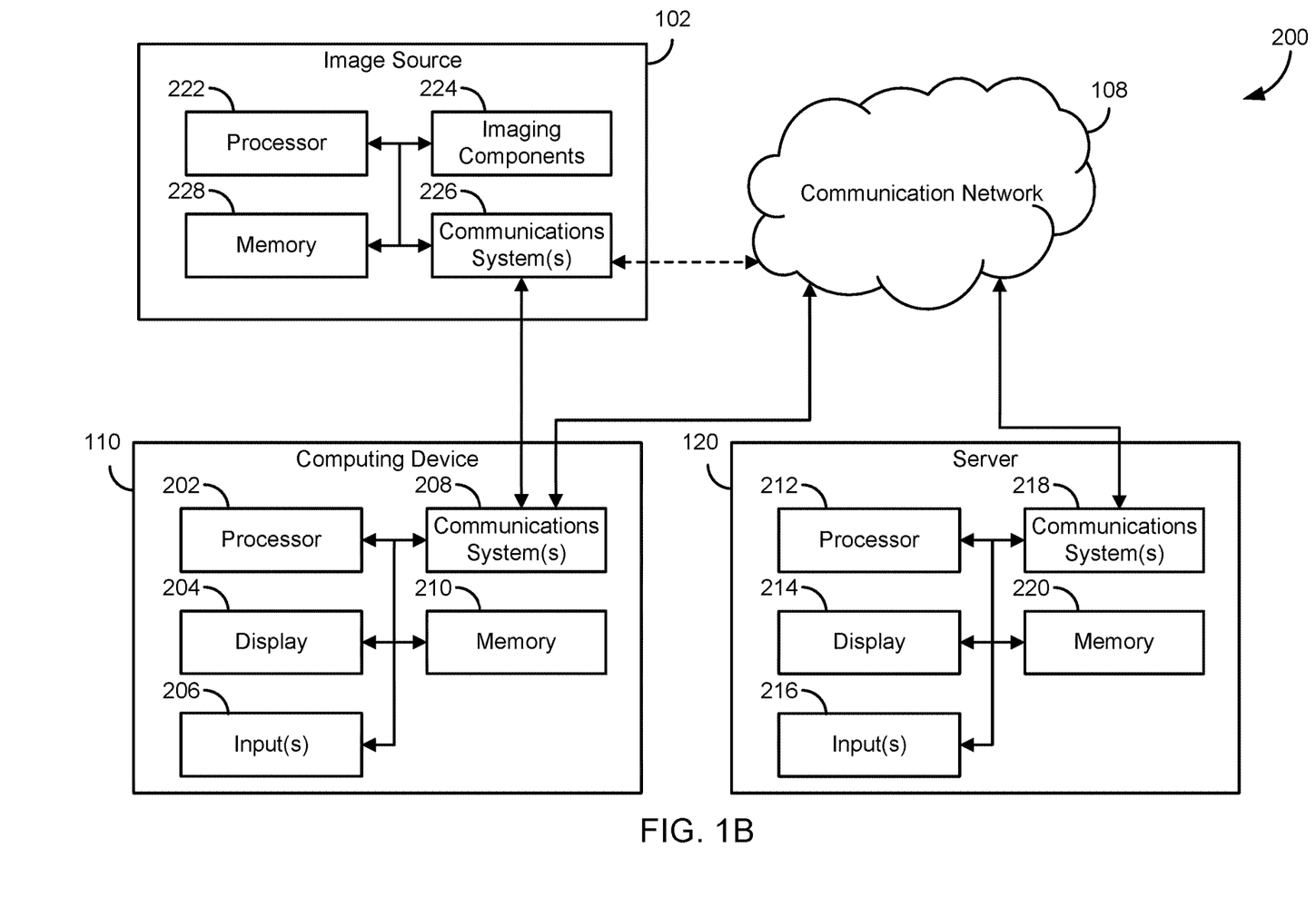
FIG. 1B is a block diagram showing further details of one, non-limiting example of the system of FIG. 1.

FIG. 1B shows an example of hardware 200 that can be used to implement the image source 102, computing device 110, and/or server 120 in accordance with some aspects of the disclosed subject matter. As shown in FIG. 2, in some configurations, the computing device 110 can include a processor 202, a display 204, one or more inputs 206, one or more communication systems 208, memory 210. In some configurations, the processor 202 can be any suitable hardware processor or combination of processors, such as a central processing unit (CPU), a graphics processing unit (GPU), and the like. In some configurations, the display 204 can include any suitable display devices, such as a computer monitor, a touchscreen, a television, etc. In some configurations, the inputs 206 can include any of a variety of suitable input devices and/or sensors that can be used to receive user input, such as a keyboard, a mouse, a touchscreen, a microphone, and the like.

In some configurations, the communications systems 208 can include a variety of suitable hardware, firmware, and/or software for communicating information over the communication network 108 and/or any other suitable communication networks. For example, the communications systems 208 can include one or more transceivers, one or more communication chips and/or chip sets, etc. In a more particular example, the communications systems 208 can include hardware, firmware and/or software that can be used to establish a Wi-Fi connection, a Bluetooth connection, a cellular connection, an Ethernet connection, etc.

In some configurations, the memory 210 can include any suitable storage device or devices that can be used to store instructions, values, etc., that can be used, for example, by the processor 202 to present content using the display 204, to communicate with the server 120 via the communications system(s) 208, and the like. The memory 210 can include any of a variety of suitable volatile memory, non-volatile memory, storage, or any suitable combination thereof. For example, the memory 210 can include RAM, ROM, EEPROM, one or more flash drives, one or more hard disks, one or more solid state drives, one or more optical drives, etc. In some configurations, the memory 210 can have encoded thereon a computer program for controlling operation of the computing device 110. In such configurations, the processor 202 can execute at least a portion of the computer program to present content (e.g., MRI images, user interfaces, graphics, tables, and the like), receive content from the server 120, transmit information to the server 120, and the like.

In some configurations, the server 120 can include a processor 212, a display 214, one or more inputs 216, one or more communications systems 218, and/or memory 220. In some configurations, the processor 212 can be a suitable hardware processor or combination of processors, such as a CPU, GPU, and the like. In some configurations, the display 214 can include a suitable display devices, such as a computer monitor, a touchscreen, a television, and the like. In some configurations, the inputs 216 can include a suitable input devices and/or sensors that can be used to receive user input, such as a keyboard, a mouse, a touchscreen, a microphone, and the like.

In some configurations, the communications systems 218 can include a suitable hardware, firmware, and/or software for communicating information over the communication network 108 and/or any other suitable communication networks. For example, the communications systems 218 can include one or more transceivers, one or more communication chips and/or chip sets, and the like. In a more particular example, the communications systems 218 can include hardware, firmware and/or software that can be used to establish a Wi-Fi connection, a Bluetooth connection, a cellular connection, an Ethernet connection, and the like.

In some configurations, the memory 220 can include any suitable storage device or devices that can be used to store instructions, values, and the like, that can be used, for example, by the processor 212 to present content using the display 214, to communicate with one or more computing devices 110, and the like. The memory 220 can include any of a variety of suitable volatile memory, non-volatile memory, storage, or any suitable combination thereof. For example, the memory 220 can include RAM, ROM, EEPROM, one or more flash drives, one or more hard disks, one or more solid state drives, one or more optical drives, and the like. In some configurations, the memory 220 can have encoded thereon a server program for controlling operation of the server 120. In such configurations, the processor 212 can execute at least a portion of the server program to transmit information and/or content (e.g., MRI data, results of image artifact removal, a user interface, and the like) to one or more computing devices 110, receive information and/or content from one or more computing devices 110, receive instructions from one or more devices (e.g., a personal computer, a laptop computer, a tablet computer, a smartphone, and the like).

In some configurations, the image source 102 can include a processor 222, imaging components 224, one or more communications systems 226, and/or memory 228. In some embodiments, processor 222 can be any suitable hardware processor or combination of processors, such as a CPU, GPU, and the like. In some configurations, the imaging components 224 can be any suitable components to generate image data corresponding to one or more imaging modes (e.g., T1 imaging, T2 imaging, fMRI, and the like). An example of an imaging machine that can be used to implement the image source 102 can include a conventional MRI scanner (e.g., a 1.5 T scanner, a 3 T scanner), a high field MRI scanner (e.g., a 7 T scanner), an open bore MRI scanner, and the like.

Note that, although not shown, the image source 102 can include any suitable inputs and/or outputs. For example, the image source 102 can include input devices and/or sensors that can be used to receive user input, such as a keyboard, a mouse, a touchscreen, a microphone, a trackpad, a trackball, hardware buttons, software buttons, and the like. As another example, the image source 102 can include any suitable display devices, such as a computer monitor, a touchscreen, a television, etc., one or more speakers, and the like.

In some configurations, the communications systems 226 can include any suitable hardware, firmware, and/or software for communicating information to the computing device 110 (and, in some embodiments, over the communication network 108 and/or any other suitable communication networks). For example, the communications systems 226 can include one or more transceivers, one or more communication chips and/or chip sets, and the like. In a more particular example, the communications systems 226 can include hardware, firmware and/or software that can be used to establish a wired connection using any suitable port and/or communication standard (e.g., VGA, DVI video, USB, RS-232, and the like), Wi-Fi connection, a Bluetooth connection, a cellular connection, an Ethernet connection, and the like.

In some configurations, the memory 228 can include any suitable storage device or devices that can be used to store instructions, values, image data, and the like, that can be used, for example, by the processor 222 to: control the imaging components 224, and/or receive image data from the imaging components 224; generate images; present content (e.g., MRI images, a user interface, and the like) using a display; communicate with one or more computing devices 110; and the like. The memory 228 can include any suitable volatile memory, non-volatile memory, storage, or any of a variety of other suitable combination thereof. For example, the memory 228 can include RAM, ROM, EEPROM, one or more flash drives, one or more hard disks, one or more solid state drives, one or more optical drives, and the like. In some configurations, the memory 228 can have encoded thereon a program for controlling operation of the image source 102. In such configurations, the processor 222 can execute at least a portion of the program to generate images, transmit information and/or content (e.g., MRI image data) to one or more the computing devices 110, receive information and/or content from one or more computing devices 110, receive instructions from one or more devices (e.g., a personal computer, a laptop computer, a tablet computer, a smartphone, and the like).

In some configurations, image source 102 may generate any format of medical image data, such as an MRI, CT, ultrasound, PET, SPECT, x-ray, and the like. Medical image data includes not only data for reconstructing the image itself, which may be compressed or not, but also contains patient identification and demographic information and technical information about the exam, including image series data, acquisition or protocol information, and other details. Medical image data may also be in the form of complex image series information, such as time-resolved 2D image series, 3D volumes, and may include additional information, such as elastography data on tissue stiffness or other diagnostic notations.

Figure 1C:
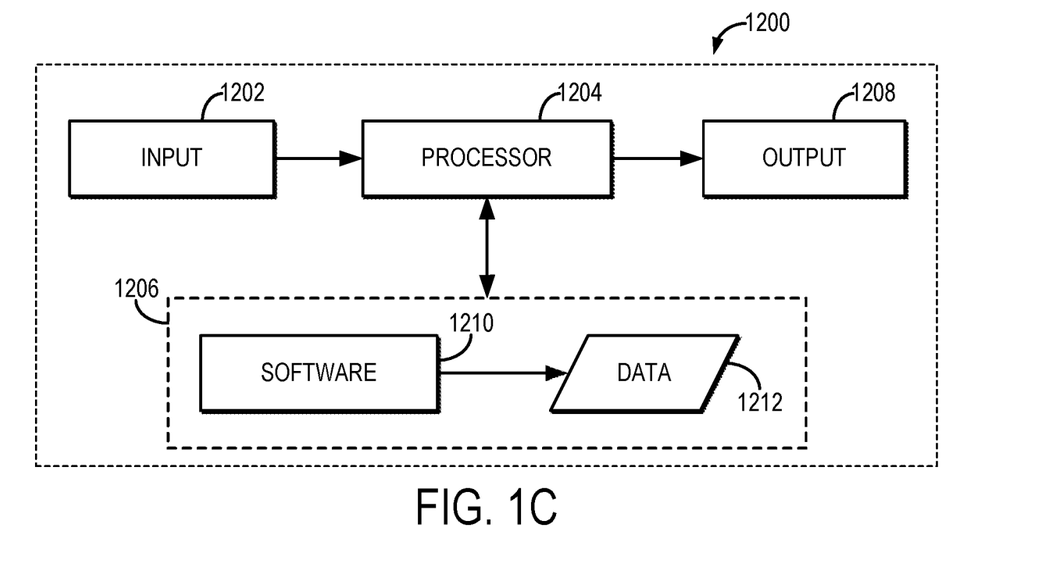
FIG. 1C is a block diagram of an example computer system that can implement the methods described in the present disclosure.

Referring now to FIG. 1C, a block diagram of an example of a computer system 1200 that can perform the methods described in the present disclosure is shown. The computer system 1200 generally includes an input 1202, at least one hardware processor 1204, a memory 1206, and an output 1208. Thus, the computer system 1200 is generally implemented with a hardware processor 1204 and a memory 1206.

In some embodiments, the computer system 1200 can be a workstation, a notebook computer, a tablet device, a mobile device, a multimedia device, a network server, a mainframe, one or more controllers, one or more microcontrollers, or any other general-purpose or application-specific computing device.

The computer system 1200 may operate autonomously or semi-autonomously, or may read executable software instructions from the memory 1206 or a computer-readable medium (e.g., a hard drive, a CD-ROM, flash memory), or may receive instructions via the input 1202 from a user, or any another source logically connected to a computer or device, such as another networked computer or server. Thus, in some embodiments, the computer system 1200 can also include any suitable device for reading computer-readable storage media.

In general, the computer system 1200 is programmed or otherwise configured to implement the methods and algorithms described in the present disclosure. For instance, the computer system 1200 can be programmed to implement the methods described in the present disclosure.

The input 1202 may take any suitable shape or form, as desired, for operation of the computer system 1200, including the ability for selecting, entering, or otherwise specifying parameters consistent with performing tasks, processing data, or operating the computer system 1200. In some aspects, the input 1202 may be configured to receive data, such as data acquired with an MRI system. Such data may be processed as described above. In addition, the input 1202 may also be configured to receive any other data or information considered useful for implementing the methods described above.

Among the processing tasks for operating the computer system 1200, the one or more hardware processors 1204 may also be configured to carry out any number of post-processing steps on data received by way of the input 1202.

The memory 1206 may contain software 1210 and data 1212, such as data acquired with an MRI system, and may be configured for storage and retrieval of processed information, instructions, and data to be processed by the one or more hardware processors 1204. In some aspects, the software 1210 may contain instructions directed to implementing the methods described in the present disclosure.

In addition, the output 1208 may take any shape or form, as desired, and may be configured for displaying images, such as images reconstructed or otherwise generated using the methods described in the present disclosure, in addition to other desired information.

Figure 2:
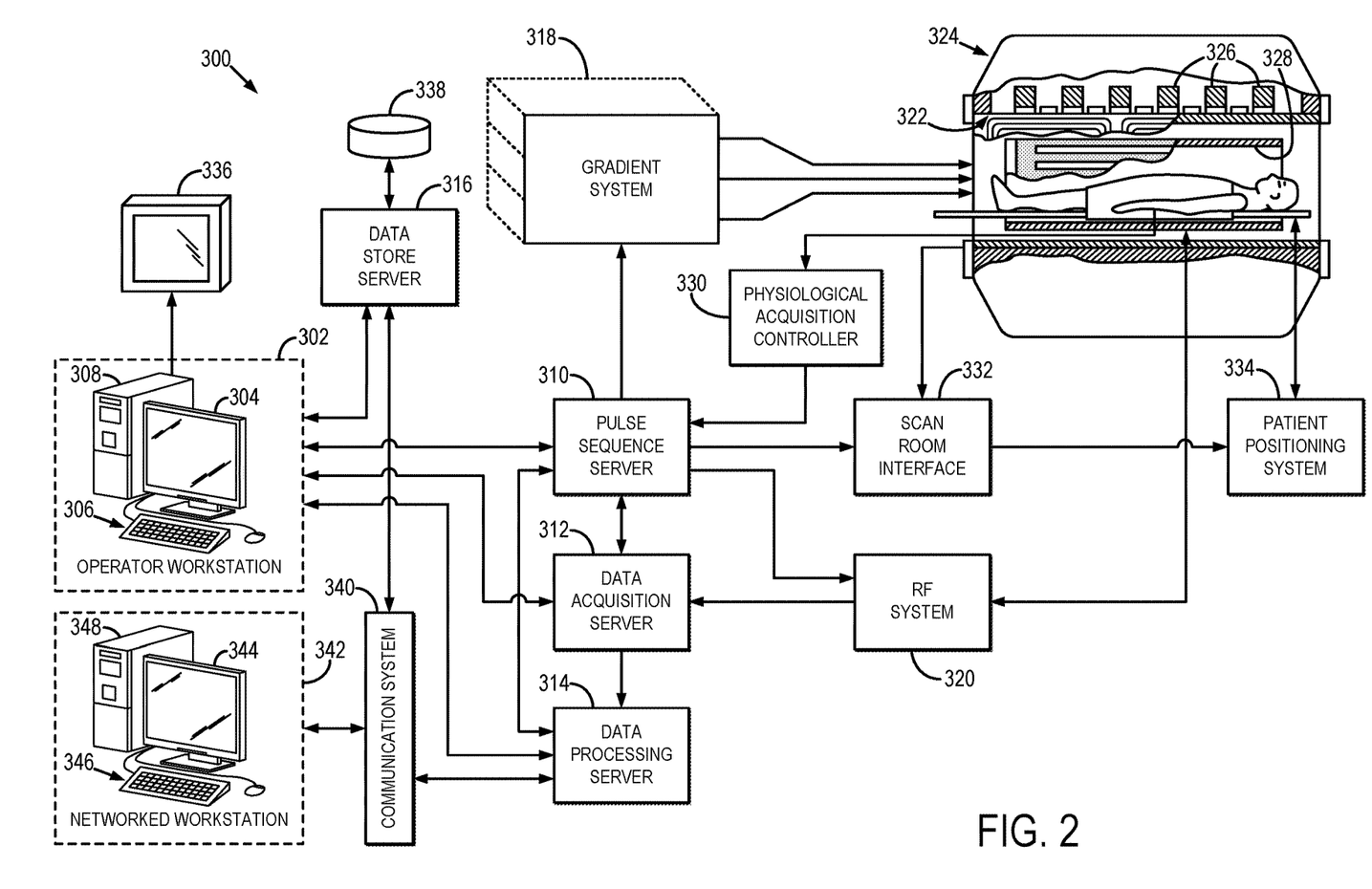
FIG. 2 is a block diagram of an example MRI system that can implement the methods described in the present disclosure.

Referring particularly now to FIG. 2, an example of an MRI system 300 that can implement the methods described here is illustrated. The MRI system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MRI system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 318, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 310 may receive patient data from a physiological acquisition controller 330. By way of example, the physiological acquisition controller 330 may receive signals from a number of different sensors connected to the patient, including electrocardiograph ("ECG") signals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MRI system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

Figure 3:
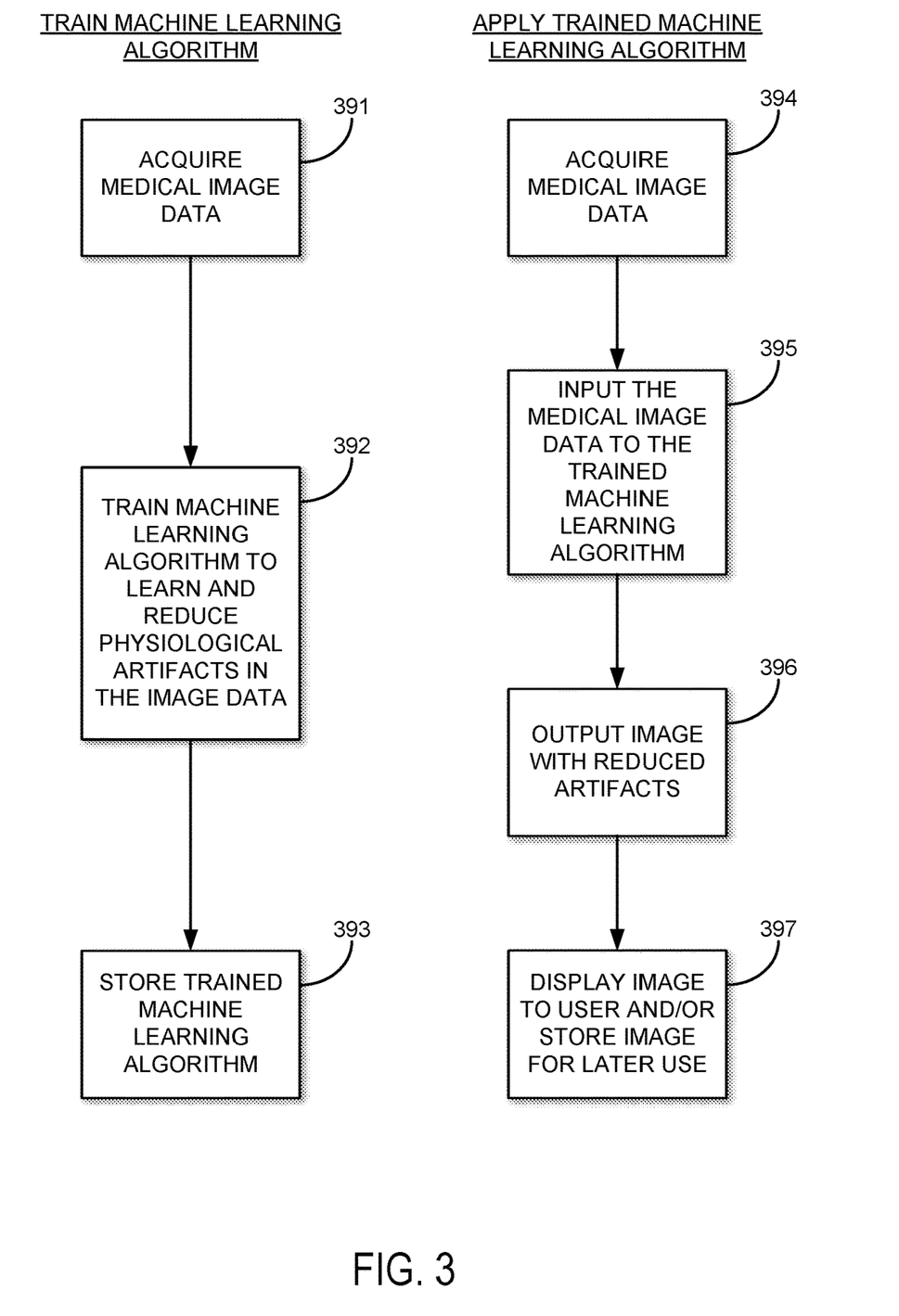
FIG. 3 is a flowchart setting forth some non-limiting examples of steps for one configuration of removing physiological image artifacts using a machine learning routine in accordance with the present disclosure.

Referring particularly to FIG. 3, a flowchart setting forth some non-limiting examples of steps for training and implementing a machine learning algorithm to generate images in which physiological artifacts are reduced or otherwise removed. The method includes training and then applying the machine learning algorithm. Training the machine learning algorithm can include acquiring or otherwise accessing previously acquired medical image data, as indicated at step 391. In one configuration, medical image data includes MR image data acquired with a rapid imaging sequence, such as an MS-EPI sequence. A machine learning algorithm is then trained on these medical image data to learn and reduce or remove the physiological artifacts in the medical image data, as indicated at step 392. As one example, the machine learning algorithm may be trained as discussed above. The trained machine learning algorithm is then stored for later use, as indicated at step 393. Storing the machine learning algorithm may include storing weights, biases, or both, which have been computed or otherwise estimated by training the machine learning algorithm on the training data. When the machine learning algorithm implements a neural network, storing the trained machine learning algorithm may include storing the particular neural network architecture to be implemented. For instance, data pertaining to the layers in the neural network architecture (e.g., number of layers, type of layers, ordering of layers, connections between layers) may be stored.

The trained machine learning algorithm is then applied to generate images in which physiological artifacts are reduced or otherwise removed. Medical image data are acquiring, or previously acquired medical image data are accessed, as indicated at step 394. As an example, the medical image data can include MR image data acquired with a rapid imaging sequence, such as an MS-EPI sequence. These medical image data are then input to the trained machine learning algorithm, as indicated at step 395. Inputting the medical image data to the trained machine learning algorithm generated output, which includes an image in which physiological artifacts have been reduced or otherwise removed, as indicated at step 396. This resulting image may be displayed for a user or stored for later use, as indicated at step 397.

Referring particularly to FIG. 4, a non-limiting example of a convolutional neural network (CNN) 400 for improving multi-shot echo planar imaging is shown. Corrupted MS-EPI image 410 may include real and imaginary channels. Corrupted image patch 415 may be selected to be a size that optimizes the CNN learning rate. The first layer of the CNN may be a convolution and rectified linear unit (RELU) layer 420. The second layer of the CNN may be a convolution, batch norm, and rectified linear unit (RELU) layer 430. Any number of layers 440 may be used, and the number of layers may be selected based upon the complexity of the physiological artifacts being removed. A fourth layer of the CNN may be a convolution, batch norm, and rectified linear unit (RELU) layer 450. A final layer of the CNN may be a convolution layer 460. An artifact-only image 470 may include real and imaginary channels and may be generated and assessed with a patch 475 for comparison to the original corrupted MS-EPI image 410.

In one non-limiting example, the corrupted MS-EPI image patch 415 was selected to be 51×51×2. 25 layers were used with each of the layers being 3×3×64 and the final layer 460 being 3×3×1. The artifact-only image patch was also selected to be 51×51×2 and included both real and imaginary channels.

The present disclosure has described one or more preferred embodiments, and it should be appreciated that many equivalents, alternatives, variations, and modifications, aside from those expressly stated, are possible and within the scope of the invention.

The invention claimed is:

1. A method for reducing image artifacts using a magnetic resonance imaging system, comprising:
    a) acquiring image data of a subject using a magnetic resonance imaging (MRI) system implementing a rapid imaging sequence;
    b) providing to a computer system a trained machine learning algorithm that has been trained on training data comprising corrupted image data and physiological artifacts in order to reconstruct images from image data such that the reconstructed images depict reduced physiological artifacts;
    c) applying the acquired image data to the trained machine learning algorithm, and generating an output that comprises one or more images reconstructed from the image data, wherein the one or more images depict reduced physiological artifacts; and
    wherein the trained machine learning algorithm is a residual machine learning algorithm that is trained on the training data to map between corrupted images and image artifacts.

2. The method of claim 1 wherein the rapid imaging sequence is a multi-shot echo planar imaging (MS-EPI) sequence.

3. The method of claim 2 wherein the physiological artifacts include shot-to-shot motion artifacts.

4. The method of claim 2 wherein the one or more reconstructed images depict contrast weighting associated with gradient-echo (GRE) contrast.

5. The method of claim 1 wherein the residual machine learning algorithm comprises a convolutional neural network.

6. The method of claim 1 wherein the physiological artifacts include at least one of patient motion, physiological noise, or phase variations.

7. A system for reducing image artifacts using a magnetic resonance imaging system, comprising:
    a computer system configured to
    i) acquire image data of a subject using a magnetic resonance imaging (MRI) system implementing a rapid imaging sequence;
    ii) implement a trained machine learning algorithm that has been trained on training data comprising corrupted image data and physiological artifacts in order to reconstruct images from image data such that the reconstructed images depict reduced physiological artifacts;
    iii) apply the acquired image data to the trained machine learning algorithm, and generate an output that comprises one or more images reconstructed from the image data, wherein the one or more images depict reduced physiological artifacts; and wherein the trained machine learning algorithm is a residual machine learning algorithm that is trained on the training data to map between corrupted images and image artifacts.

8. The system of claim 7 wherein the rapid imaging sequence is a multi-shot echo planar imaging (MS-EPI) sequence.

9. The system of claim 8 wherein the physiological artifacts include shot-to-shot motion artifacts.

10. The system of claim 8 wherein the one or more reconstructed images depict contrast weighting associated with gradient-echo (GRE) contrast.

11. The system of claim 7 wherein the residual machine learning algorithm comprises a convolutional neural network.

12. The system of claim 7 wherein the physiological artifacts include at least one of patient motion, physiological noise, or phase variations.

13. A non-transitory computer-readable medium storing instructions, the instructions comprising: A method for reducing image artifacts using a magnetic resonance imaging system, comprising:

one or more instructions that, when executed by one or more processors, cause the one or more processors to:
  i) acquire image data of a subject using a magnetic resonance imaging (MRI) system implementing a rapid imaging sequence;
  ii) implement a trained machine learning algorithm that has been trained on training data comprising corrupted image data and physiological artifacts in order to reconstruct images from image data such that the reconstructed images depict reduced physiological artifacts;
  iii) apply the acquired image data to the trained machine learning algorithm, and generate an output that comprises one or more images reconstructed from the image data, wherein the one or more images depict reduced physiological artifacts, and wherein the trained machine learning algorithm is a residual machine learning algorithm that is trained on the training data to map between corrupted images and image artifacts.

14. The non-transitory computer-readable medium of claim 13 wherein the rapid imaging sequence is a multi-shot echo planar imaging (MS-EPI) sequence.

15. The non-transitory computer-readable medium of claim 14 wherein the physiological artifacts include shot-to-shot motion artifacts.

16. The non-transitory computer-readable medium of claim 14 wherein the one or more reconstructed images depict contrast weighting associated with gradient-echo (GRE) contrast.

17. The non-transitory computer-readable medium of claim 13 wherein the residual machine learning algorithm comprises a convolutional neural network.

18. The non-transitory computer-readable medium of claim 13 wherein the physiological artifacts include at least one of patient motion, physiological noise, or phase variations.

* * * * *

UNITED STATES PATENT AND TRADEMARK OFFICE
CERTIFICATE OF CORRECTION

PATENT NO. : 11,391,803 B2
APPLICATION NO. : 16/976997
DATED : July 19, 2022
INVENTOR(S) : Berkin Bilgic et al.

It is certified that error appears in the above-identified patent and that said Letters Patent is hereby corrected as shown below:

In the Specification

Column 1, Lines 18-21:
"This invention was made with government support under EB02061302 and EB01 733704 awarded by the National Institutes of Health. The government has certain rights in the invention."

Should be:
--This invention was made with government support under EB020613, and EB017337 awarded by the National Institutes of Health. The government has certain rights in the invention.--.

Signed and Sealed this
Ninth Day of May, 2023

Katherine Kelly Vidal
*Director of the United States Patent and Trademark Office*